US009131958B2

(12) United States Patent
Lunn et al.

(10) Patent No.: US 9,131,958 B2
(45) Date of Patent: Sep. 15, 2015

(54) SEAL ASSEMBLY FOR A CANNULA

(75) Inventors: Richard M. Lunn, Kingston, MA (US);
David A. Paulk, Hopedale, MA (US);
Julie K. Tripodi, Marlborough, MA (US)

(73) Assignee: Smith & Nephew, Inc., Memphis, TN (US)

(*) Notice: Subject to any disclaimer, the term of this patent is extended or adjusted under 35 U.S.C. 154(b) by 62 days.

(21) Appl. No.: 13/332,229

(22) Filed: Dec. 20, 2011

(65) Prior Publication Data

US 2012/0089160 A1    Apr. 12, 2012

Related U.S. Application Data

(63) Continuation of application No. 11/753,094, filed on May 24, 2007, now Pat. No. 8,092,431.

(51) Int. Cl.
*A61M 5/14* (2006.01)
*A61B 17/34* (2006.01)
(Continued)

(52) U.S. Cl.
CPC ......... *A61B 17/3462* (2013.01); *A61B 17/0483* (2013.01); *A61B 17/3415* (2013.01); *A61B 17/3474* (2013.01); *A61B 2017/00862* (2013.01); *A61B 2017/349* (2013.01)

(58) Field of Classification Search
CPC ........... A61B 17/3462; A61B 17/0483; A61B 17/3415; A61B 17/349; A61B 17/2018; A61B 17/0469; A61B 2017/3466
USPC ................. 604/96.01, 164.01, 523, 264, 256, 604/167.04; 606/148, 150
See application file for complete search history.

(56) References Cited

U.S. PATENT DOCUMENTS

| 4,626,245 A | 12/1986 | Weinstein |
| 5,009,391 A | 4/1991 | Steigerwald |
| 5,041,095 A | 8/1991 | Littrell |

(Continued)

FOREIGN PATENT DOCUMENTS

| EP | 0369314 A2 | 5/1990 |
| EP | 0369314 A2 * | 5/1990 |
| EP | 1671598 A1 * | 6/2006 |

OTHER PUBLICATIONS

Patent examination report No. 1 regarding Australian patent application 2008256789 mailed Oct. 12, 2012.
(Continued)

*Primary Examiner* — Bhisma Mehta
*Assistant Examiner* — Brandy S Lee
(74) *Attorney, Agent, or Firm* — Burns & Levinson LLP; Joseph M. Maraia (57) ABSTRACT

The present disclosure relates to a seal assembly for a cannula. The cannula includes a housing having a proximal portion and a distal portion. The seal assembly is located in the proximal portion of the housing and includes a first seal including a first tri-slit, a second seal disposed co-axially and proximal to the first seal and including a second tri-slit, and a third seal disposed co-axially to the first seal and the second seal and including a central opening. A cap is coupled to the proximal portion of the housing and adjacent the third seal and includes a plurality of suture retaining features, such as tabs, for management of sutures during surgery. Fluid leakage out of the cannula, during surgery, is substantially reduced due to the leakage being limited to a channel defined by the first tri-slit, the second tri-slit, and the central opening.

36 Claims, 6 Drawing Sheets

(51) Int. Cl.
  *A61B 17/04* (2006.01)
  *A61B 17/00* (2006.01)

(56) References Cited

U.S. PATENT DOCUMENTS

| | | | |
|---|---|---|---|
| 5,437,646 A * | 8/1995 | Hunt et al. | 604/167.04 |
| 5,496,289 A | 3/1996 | Wenstrom, Jr. | |
| 5,643,227 A * | 7/1997 | Stevens | 604/264 |
| 6,024,729 A * | 2/2000 | Dehdashtian et al. | 604/256 |
| 6,551,283 B1 | 4/2003 | Guo et al. | |
| 2005/0033342 A1 | 2/2005 | Hart et al. | |
| 2005/0065535 A1 | 3/2005 | Morris et al. | |
| 2005/0070851 A1 | 3/2005 | Thompson et al. | |

OTHER PUBLICATIONS

International Search Report and Written Opinion for PCT/US2008/064612 dated Jun. 11, 2008.

Office Action for European Patent Application EP 08756 155.1-2310 mailed Sep. 16, 2011.

* cited by examiner

SEAL ASSEMBLY FOR A CANNULA

BACKGROUND OF THE INVENTION

1. Field of the Invention

The present disclosure relates generally to medical and surgical devices, and more specifically to seal assemblies for cannulas.

2. Related Art

Arthroscopic or, more generally, endoscopic surgical procedures enable closed surgery to be performed via portals through which a variety of elongated instruments may be passed to gain access to an internal surgical work site. Very often a disposable cannula is inserted into the portal in order to provide a convenient passageway through which various instruments may be passed. Because many arthroscopic procedures require the use of pressurized fluid to distend and irrigate the joint being operated upon, the cannula must provide a sealed passageway in order to enable instruments to be passed into and out of the cannula while maintaining a fluid seal whether or not an instrument is in the cannula passageway. The sealing of such cannula passageways is usually accomplished by one or more elastomeric membranes attached to the proximal end of the elongated cannula.

Figure 1:
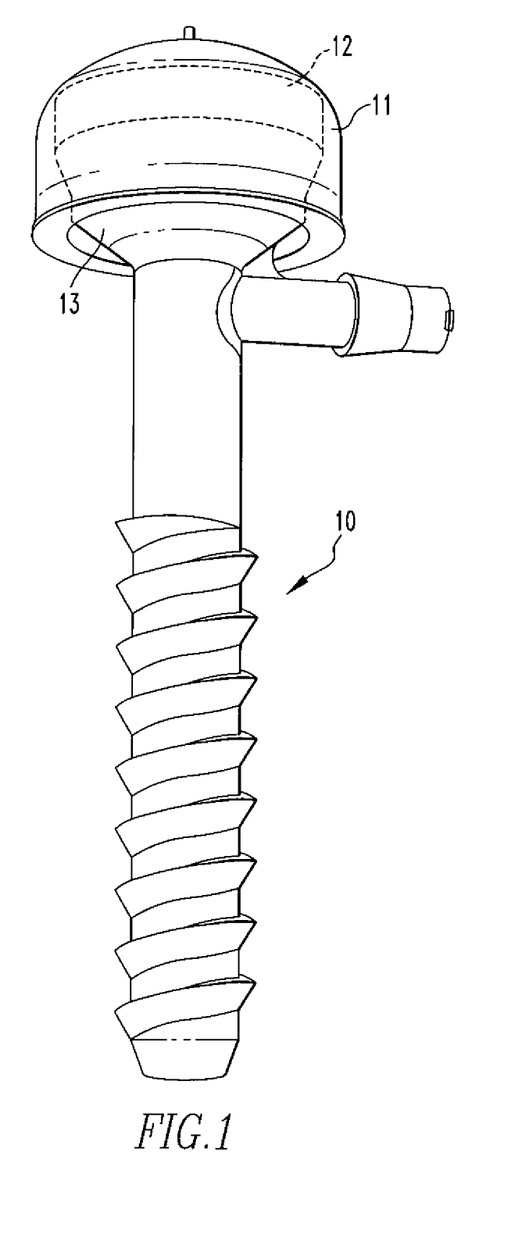
FIG. 1 shows a perspective view of a prior art cannula having a spray shield coupled to the proximal end of the cannula.

Since the fluid at the work site is pressurized, care must be taken to avoid leakage during the time the instrument is being inserted. Current seal assemblies for use in cannulas leak excessively and improvement on the amount of leakage out of the cannula is desired. In addition, upon insertion of an instrument into an opening on the seals of current models, fluid sprays out of the opening. In order to prevent this from occurring, the seal is covered by placing a spray shield on the proximal end of the cannula. FIG. 1 shows a current cannula model 10 that has a spray shield 11 covering the seal assembly 12 at the proximal end 13 of the cannula 10. However, the size of the spray shield 11 makes it difficult for the surgeon to work in tight operative spaces. Therefore, a sealing assembly that minimizes this problem is also needed.

Furthermore, the variety of instruments which must be inserted through the cannula seal includes instruments of varying sizes and configurations. While the instrument shafts are usually cylindrical, some instruments may have unusually large or sharp distal tips which may cut a seal element upon the insertion or extraction of the instrument thus making it less suitable for subsequent instruments which must be inserted during the same surgical procedure. It is desirable, therefore, to devise a sealing cannula which minimizes this problem.

Finally, in addition to instruments, sutures may also be passed through the seal assembly. In fact, the management of these sutures has become critical to the technical success of the surgery. Indeed, tangled sutures can terminate an arthroscopic procedure. Therefore, an approach to suture management is also needed.

SUMMARY OF THE INVENTION

The present disclosure relates to a seal assembly for a cannula. The cannula includes a housing having a proximal portion and a distal portion. The seal assembly is located in the proximal portion of the housing and includes a first seal including a first tri-slit, a second seal disposed co-axially and proximal to the first seal and including a second tri-slit, and a third seal disposed co-axially to the first seal and the second seal and including a central opening having a diameter of between about 0.060 inches to about 0.120 inches. In an embodiment, a cap is coupled to the proximal portion of the housing and adjacent the third seal and includes a plurality of suture retaining features, such as tabs, for management of sutures during surgery. In another embodiment, the seal assembly further includes a space located between the second seal and the third seal. In yet another embodiment, the first tri-slit and the second tri-slit are offset by an angle α, which is about 180°. In a further embodiment, the first tri-slit, the second tri-slit and the central opening define a channel passing through the seal assembly. Fluid leakage during surgery is limited to the channel. In yet a further embodiment, the first seal and the second seal are configured to form a seal against sutures and the third seal is configured to form a seal against shafted instruments. In an embodiment, the third seal comprises a synthetic material. In another embodiment, the third seal comprises a polymer, such as polyisoprene.

The present disclosure also relates to a seal assembly having a first seal including a first tri-slit and at least one interlocking member, a second seal disposed co-axially and proximal to the first seal, the second seal including a second tri-slit and at least one interlocking member, and a third seal disposed co-axially and proximal to the first seal and the second seal, the third seal including a central opening. The interlocking member of the first seal and the interlocking member of the second seal interlock with each other. In an embodiment, the first seal and the second seal both include multiple interlocking members, wherein the interlocking members of the first seal and the interlocking members of the second seal interlock with each other. The interlocking between the interlocking member of the first seal and the interlocking member of the second seal facilitates positioning of the first tri-slit and the second tri-slit at an angle α, which is about 180°, relative to each other.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention. In the drawings.

DETAILED DESCRIPTION OF THE EMBODIMENTS

The following description of the preferred embodiment(s) is merely exemplary in nature and is in no way intended to limit the invention, its application, or uses.

Figure 2:
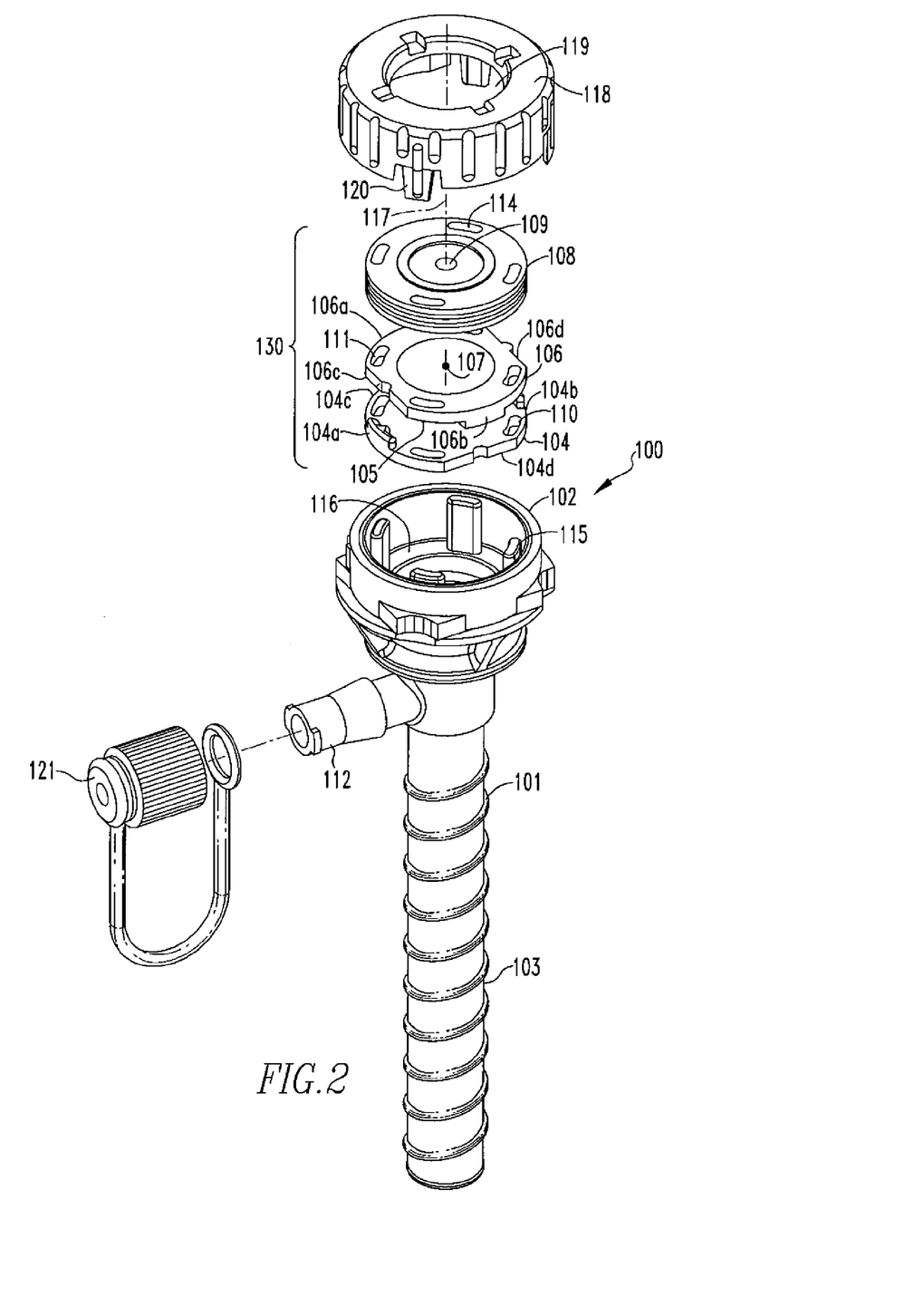
FIG. 2 shows an exploded perspective view of the cannula of the present disclosure.

An embodiment of a cannula of the present disclosure is illustrated in FIG. 2 and designated generally by reference number 100. The cannula includes a seal assembly for substantially reducing the amount of fluid leakage from the cannula and specifically for forming a seal against sutures and shafted instruments.

Figure 3A:
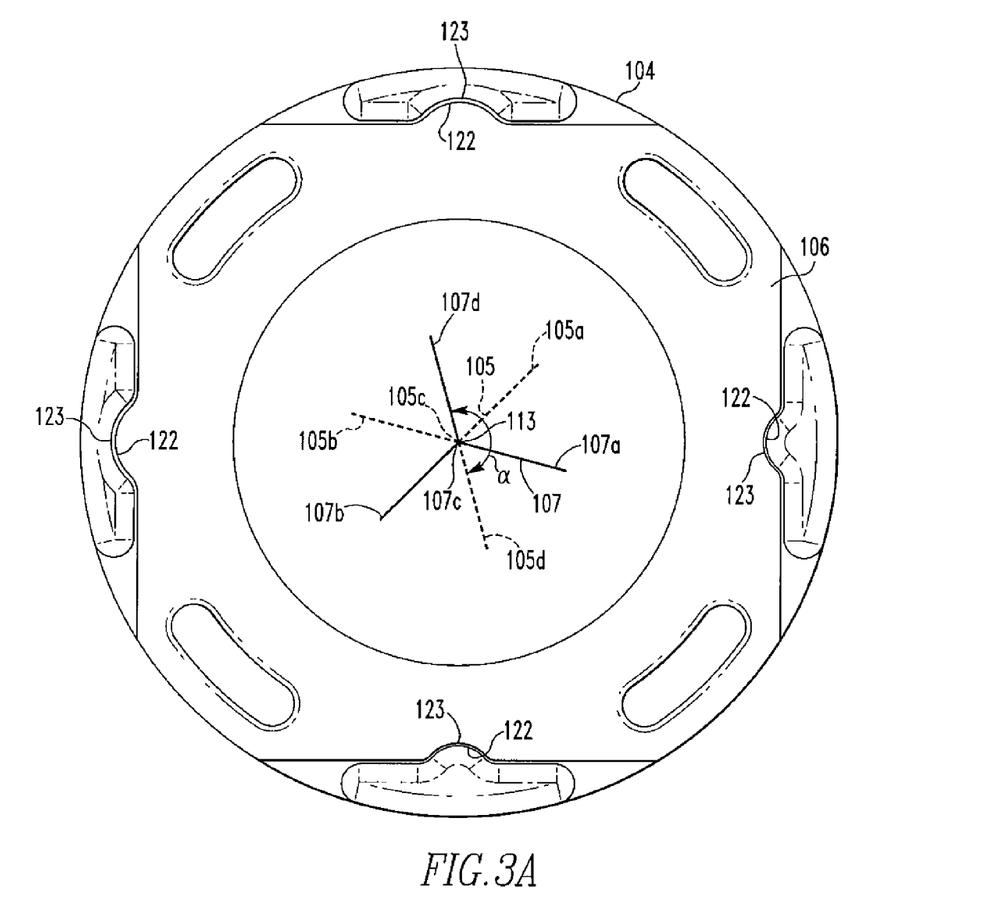
FIG. 3A shows a top view of the first and second seals of the seal assembly of the present disclosure.

The cannula 100, which is plastic, but could be made from other material known to one of ordinary skill in the art, includes a housing 101 having a proximal portion 102 and a distal portion 103. Near the proximal portion 102, an outflow tube 112 provides a means for removing fluid from the inner lumen of the distal portion 103 during surgery. Although, it is also within the scope of this disclosure that the tube 112 may be used as an inflow tube for supplying fluid to the inner lumen of the distal portion 130 during surgery. A cover 121 is detachably coupled to the inflow tube 112 for closing off the inflow tube while the cannula 100 is not in use. Located in the proximal portion 102 is a seal assembly 130. The seal assembly 130 includes a first seal 104 having a first tri-slit 105, a second seal 106 that is disposed co-axially and proximal to the first seal 104 and includes a second tri-slit 107, and a third seal 108 that is disposed coaxially and proximal to the first seal 104 and the second seal 106 and includes a central opening 109. The first seal 104 and the second seal 106 both have four sides (104a-d, 106a-d). The seals 104,106 also have openings 110,111 that extend through the seals 104,106. The second seal 106 sits proximal to the first seal 104 such that no space exists between the seals 104,106, the openings 110,111 of both seals 104,106 are aligned, and the tri-slits 105,107 are offset by an angle α, or about 180°, as is further shown in FIG. 3A. Sides (104a-b, 106a-b) and sides (104c-d, 106c-d) of the seals 104,106 are made to interlock with each other. For example, as shown in FIG. 3A, the seals 104,106 include interlocking members, such as tabs 122 and detents 123, which interlock with one another. The tabs 122 and detents 123 alternate with regards to the seals 104,106 that they are located on. This interlocking feature facilitates positioning of the tri-slits 105,107 at an angle, about 180°, relative to each other each time the seals 104,106 are assembled together. Other interlocking features, known to one of ordinary skill in the art, may be used.

Figure 3B:
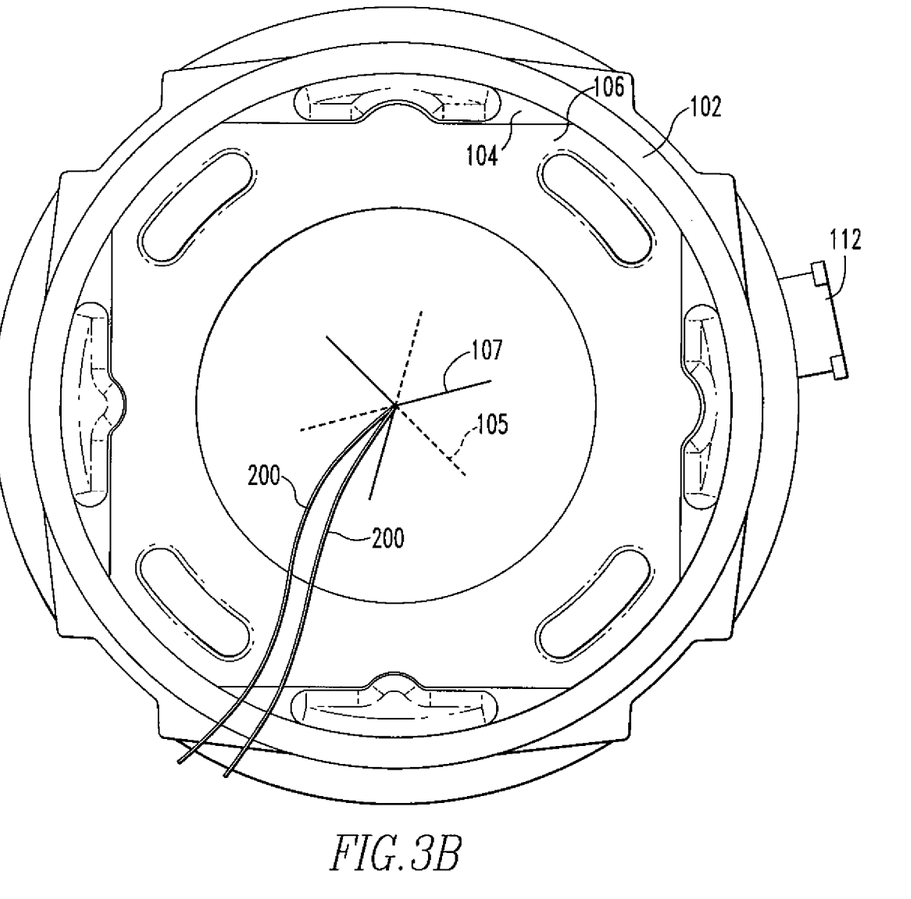
FIG. 3B shows a top view of the first and second seals of the present disclosure showing suture coming out of the tri-slits.

Also shown in FIG. 3A, the tri-slits 105,107 are of a Y-shaped configuration with each slit 105,107 defining a pair of slit arms (105a-b, 107a-b) joined together at one end 105c,107c and forming an obtuse angle as shown. Thus, they each define an arrow pointing in an opposed direction to each other and also define a pair of intersection points 113, forming a channel, as further discussed below, that that extends completely through both seals 104,106. Added to each pair of arms (105a-b, 107a-b) are slit legs 105d, 107d, which are located at an angle α, or about 180°, from each other. As is shown in FIG. 3B, the tri-slits 105,107 provide a seal against the sutures 200 by having a channel, as further discussed below, that has the smallest possible opening to the sutures 200 and substantially reduces the amount of fluid leaving the cannula. For the purposes of this disclosure, both the first 104 and the second 106 seals are made from silicon. However, other material known to one of ordinary skill in the art could be used, including, but not limited to, rubber, vinyl, polyurethane elastomers, or a combination of components, including styrene-ethylene-butylene-styrene (SEBS) block co-polymers, polyolefins, mineral oils, and silicone oils.

Figure 4:
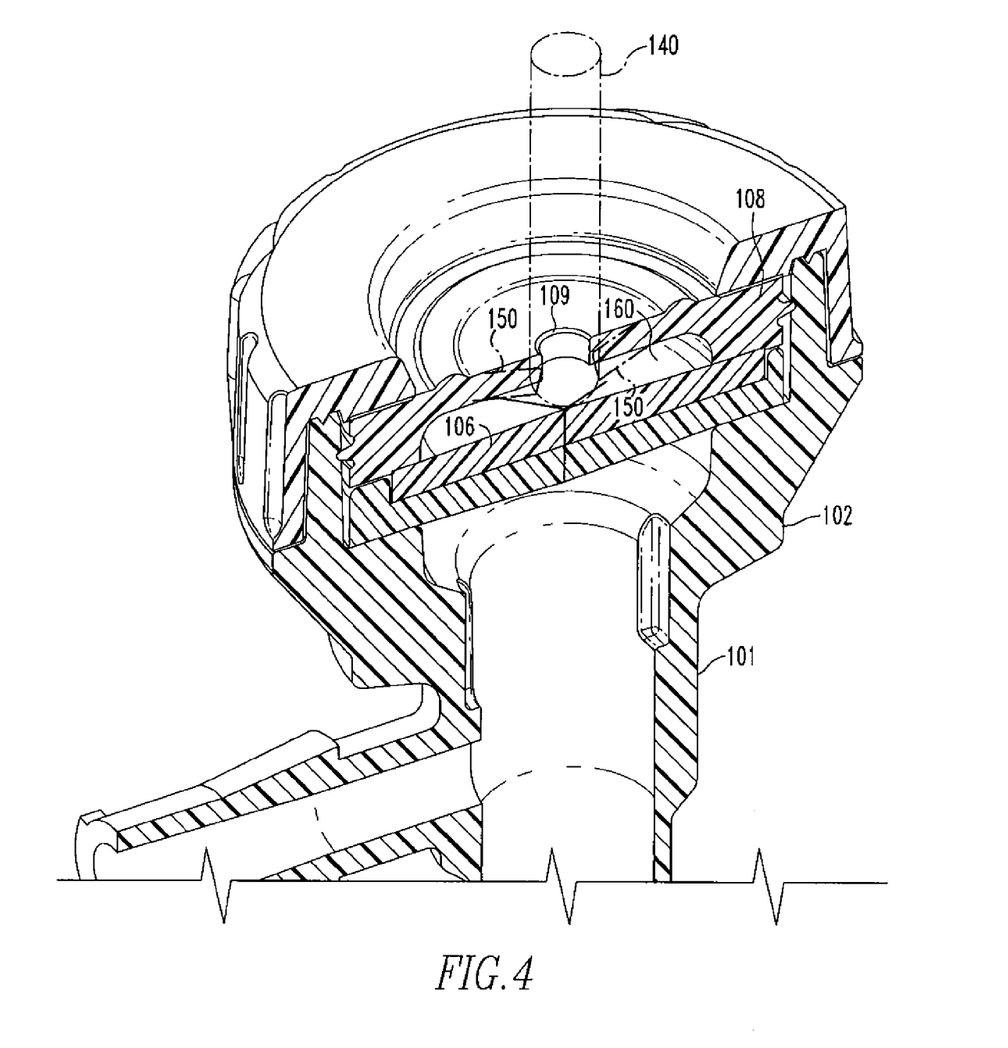
FIG. 4 shows a cross-sectional perspective view of the proximal portion of the cannula of the present disclosure.

The third seal 108 is located proximal to the first 104 and second 106 seals and includes a central opening 109, along with four other openings 114 that are located around the outer diameter of the seal 108. The seal 108 is in a co-axial relationship with the first 104 and second 106 seal such that the central opening 109 is aligned with the center 113 of the tri-slits 105,107 and the openings 114 on the outer diameter are aligned with the openings 110,111 on the first and second seals 104,106. As shown in FIG. 4, the central opening 109, which is between about 0.060 inches to about 0.120 inches in diameter, is configured to form a seal against shafted instruments 140 that have a diameter that is larger than the opening 109. The instrument 140 is first inserted into the central opening 109, and then through the Y-slit channel of the second seal 106. Once the instrument is inserted into the opening 109, the walls 150 of the opening 109 push outward toward the second seal 106, yet remain against the shaft of the instrument 140 to create a seal against any fluid that may flow through the tri-slits 105,107 and towards the third seal 108. For the purposes of this disclosure, the central opening 109 is round, but it could be of another shape. The third seal 108 is manufactured from a polymer material, specifically polyisoprene, to substantially reduce the amount of tearing or wear as a result of insertion and/or withdrawal of sharp instruments. Other natural or synthetic materials known to one of ordinary skill in the art, and that would substantially reduce the amount of tear or wear, could also be used. These materials include, but are not limited to, silicone, rubber, vinyl, polyurethane elastomers, or a combination of components, including styrene-ethylene-butylene-styrene (SEBS) block co-polymers, polyolefins, mineral oils, and silicone oils.

As mentioned above in FIG. 1, upon insertion of an instrument into an opening on the seals of current cannulas, fluid sprays out of the opening. In order to prevent this from occurring, the seal is covered by placing a spray shield on the proximal end of the cannula. This additional step is eliminated in the present disclosure by integrating the spray shield, which in this disclosure is the third seal 108, into the cannula. Without the spray shield covering the proximal portion of the cannula, the overall size of the cannula 100 is smaller, thereby making it easier for the surgeon to work in tight operative spaces.

In addition to eliminating the step of adding a spray shield onto the proximal portion, the cannula 100 of the present disclosure also substantially reduces the amount of fluid spray that occurs outside of the cannula 100. FIG. 4 shows a space 160 that is located between the second seal 106 and the third seal 108. This space 160 allows for a substantial reduction in the amount of fluid spray that occurs outside of the cannula 100 by causing some of the fluid that would otherwise be sprayed outside of the cannula 100 to be reflected back toward the second seal 106. In addition to causing a reflection of the fluid, the space 160 also substantially reduces the force required to insert surgical instruments 140 by allowing the walls 150 of the opening to have the space needed to push outward toward the second seal 106. If this space wasn't present and the third seal 108 was against the second seal 106, there would be no space to allow the walls 150 to push outward and a greater amount of force would therefore be required to insert the instrument 140.

The seal assembly 130 is placed in the proximal portion 102 of the housing 101 such that the openings (110,111,114) of the seals (104,106,108) are placed over columns 115 that are located along the inside perimeter 116 of the proximal portion 102. These columns 115 provide support for the seals (104,106,108).

A plastic cap 118 is coupled to the proximal portion 102 of the housing 101 and is adjacent to the third seal 108. The cap 118 may be made from another material known to one of ordinary skill in the art. Having the cap 118 on the proximal portion 102 of the housing 101 compresses the seal assembly 130 and limits fluid leakage during surgery to a channel 117 defined by the first tri-slit 105, second tri-slit 107, and central opening 109, thereby substantially reducing the amount of fluid leakage out of the cannula 100. The cap 118 includes a central opening 119 and a plurality of suture retaining features 120, or tabs, for the management of multiple strands of sutures during surgery.

Figure 5:
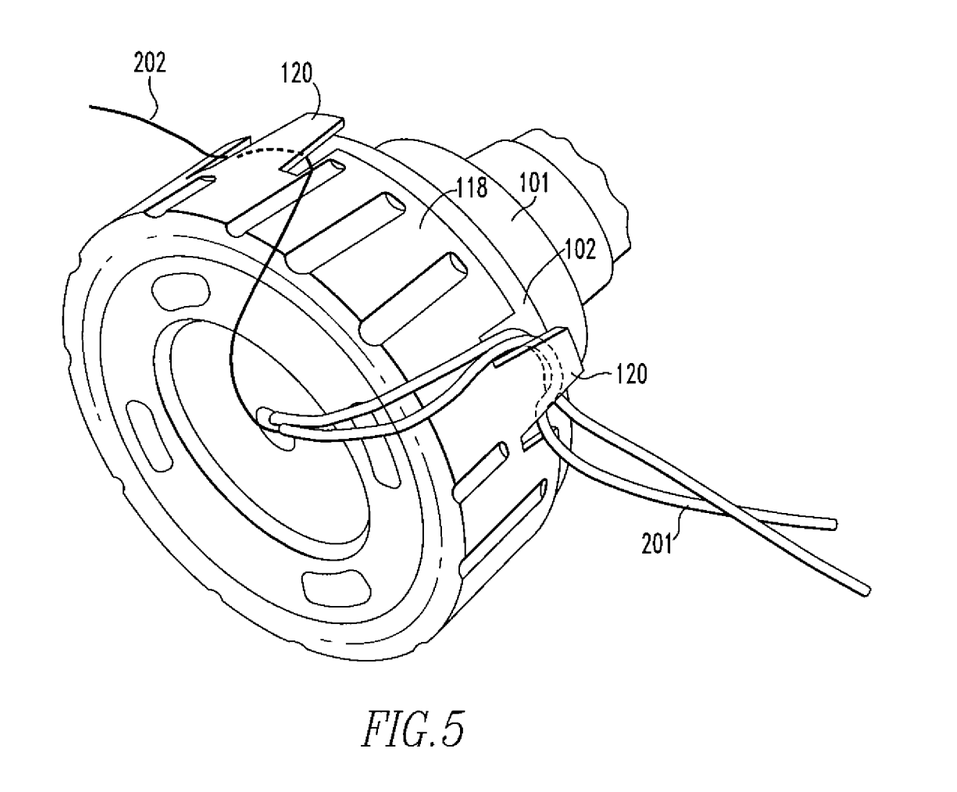
FIG. 5 shows a perspective view of the cap of the present disclosure as located on the proximal portion of the cannula.

There are several advantages for having the tabs 120 on the cap 118. As shown in FIG. 5, having multiple tabs 120 on the cap 118 allows for different strands of suture 201, 202 to be simultaneously arranged in separate positions. In addition, the tabs 120 are molded into the cap 118, which avoids the need for an accessory device and/or a modification to the housing 101 by the surgeon to manage the sutures 201,202. Furthermore, the tab length extends past the proximal portion 102 of the housing 101 to allow the capture of a suture 201,202 that is placed behind the tab 120 and drawn upwards. Additionally, the tabs 120 are tapered to maintain secure contact with suture strands of various sizes, such as strands 201 and 202. Finally, a suture 201,202 is easily removed once it is secured to the tab 120 without damage to the suture 201,202 or housing 101. It is within the scope of this disclosure that the number, size, shape, length, orientation, and thickness of the tabs 120 could be adjusted to make for alternative embodiments.

As various modifications could be made to the exemplary embodiments, as described above with reference to the corresponding illustrations, without departing from the scope of the present disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A seal assembly for a cannula, the cannula comprising a housing having a proximal portion and a distal portion, the seal assembly comprising:
   a first seal including a first tri-slit;
   a second seal disposed co-axially and proximal to the first seal, the second seal including a second tri-slit; and
   a third seal disposed co-axially and proximal to the first seal and the second seal, the third seal including:
      a central opening;
      a first portion including the central opening and extending radially outward from the central opening, the first portion having a first thickness; and
      a second portion extending radially with respect to the central opening from the radial periphery of the first portion, the second portion having a second thickness greater than the first thickness; and
   a space located between the second seal and the first portion of the third seal and having a thickness given by at least the difference in thickness of the first and second portions of the third seal;
   wherein the space is present absent insertion of an object within the second and third seals; and
   wherein the seal assembly is located in the proximal portion of the housing.

2. The seal assembly of claim 1 further comprising a cap coupled to the proximal portion of the housing and adjacent to the third seal.

3. The seal assembly of claim 2 wherein the cap comprises a plurality of suture retaining features for management of sutures during a surgery.

4. The seal assembly of claim 3 wherein the suture retaining features comprise tabs.

5. The seal assembly of claim 1 wherein the first tri-slit and the second tri-slit are offset by an angle $\alpha$.

6. The seal assembly of claim 5 wherein the angle $\alpha$ is about 180°.

7. The seal assembly of claim 1 wherein the first tri-slit, the second tri-slit, and the central opening define a channel passing through the seal assembly.

8. The seal assembly of claim 1 wherein the first seal and the second seal are configured to form a seal against sutures.

9. The seal assembly of claim 1 wherein the third seal is configured to form a seal against shafted instruments.

10. The seal assembly of claim 1 wherein the central opening comprises a diameter of between about 0.060 inches to about 0.120 inches.

11. The seal assembly of claim 1 wherein the third seal comprises a synthetic material.

12. The seal assembly of claim 1 wherein the third seal comprises a polymer material.

13. The seal assembly of claim 12 wherein the polymer material comprises polyisoprene.

14. The seal assembly of claim 1, wherein the first and second seals are in contact at about a longitudinal axis of the assembly absent insertion of an object.

15. The seal assembly of claim 1, wherein the first and second thicknesses extend distally from a proximal surface of the third seal.

16. A cannula comprising:
   a housing having a proximal portion and a distal portion;
   a cap coupled to the proximal portion of the housing; and
   a seal assembly located in the proximal portion of the housing and adjacent the cap, the seal assembly comprising:
      a first seal including a first tri-slit,
      a second seal disposed co-axially and proximal to the first seal, the second seal including a second tri-slit;
      a third seal disposed co-axially and proximal to the first seal and the second seal, the third seal including:
      a central opening;
      a first portion including the central opening and extending radially outward from the central opening, the first portion having a first thickness; and
      a second portion extending radially with respect to the central opening from the radial periphery of the first portion, the second portion having a second thickness greater than the first thickness; and
      a space located between the second seal and the first portion of the third seal and having a thickness given by at least the difference in thickness of the first and second portions of the third seal;
      wherein the space is present absent insertion of an object within the second and third seals.

17. The cannula of claim 16 wherein the cap comprises a plurality of suture retaining features for management of sutures during a surgery.

18. The cannula of claim 17 wherein the suture retaining features comprise tabs.

19. The cannula of claim 16 wherein the first tri-slit and the second tri-slit are offset by an angle $\alpha$.

20. The cannula of claim 19 wherein the angle $\alpha$ is about 180°.

21. The cannula of claim 16 further comprising a channel defined by the first tri-slit, the second tri-slit, and the central opening, wherein fluid leakage during surgery is limited to the channel.

22. The cannula of claim 16 wherein the first seal and the second seal are configured to form a seal against sutures.

23. The cannula of claim 16 wherein the third seal is configured to form a seal against shafted instruments.

24. The cannula of claim 16 wherein the central opening comprises a diameter of between about 0.060 inches and about 0.120 inches.

25. The cannula of claim 16 wherein the third seal comprises a synthetic material.

26. The cannula of claim 16 wherein the third seal comprises a polymer material.

27. The cannula of claim 26 wherein the polymer material comprises polyisoprene.

28. The cannula of claim 16, wherein the first and second seals are in contact at about a longitudinal axis of the assembly absent insertion of an object.

29. The cannula of claim 16, wherein the first and second thicknesses extend distally from a proximal surface of the third seal.

30. A seal assembly comprising:
    a first seal including a first tri-slit and at least one interlocking member;
    a second seal disposed co-axially and proximal to the first seal, the second seal including a second tri-slit and at least one interlocking member,
    a third seal disposed co-axially and proximal to the first seal and the second seal, the third seal including:
        a central opening;
        a first portion including the central opening and extending radially outward from the central opening, the first portion having a first thickness; and
        a second portion extending radially with respect to the central opening from the radial periphery of the first portion, the second portion having a second thickness greater than the first thickness; and
    a space interposed between the second seal and the first portion of the third seal and having a thickness given by at least the difference in thickness of the first and second portions of the third seal;
    wherein the space is present absent insertion of an object within the second and third seals;
    wherein the interlocking member of the first seal and the interlocking member of the second seal interlock with each other.

31. The seal assembly of claim 30 wherein the first seal and the second seal both include multiple interlocking members.

32. The seal assembly of claim 31 wherein the interlocking members of the first seal and the interlocking members of the second seal interlock with each other.

33. The seal assembly of claim 30 wherein the interlocking of the interlocking member of the first seal and the interlocking member of the second seal facilitates positioning of the first tri-slit and the second tri-slit at an angle α relative to each other.

34. The seal assembly of claim 33 wherein the angle α is about 180°.

35. The seal assembly of claim 30, wherein the first and second seals are in contact at about a longitudinal axis of the assembly absent insertion of an object.

36. The seal assembly of claim 30, wherein the first and second thicknesses extend distally from a proximal surface of the third seal.

* * * * *